(12) United States Patent
Della Ciana et al.

(10) Patent No.: US 11,573,183 B2
(45) Date of Patent: Feb. 7, 2023

(54) CHEMILUMINESCENT SUBSTRATES FOR PEROXIDASE WITH EXTENDED SHELF-LIFE

(71) Applicant: CYANAGEN S.r.l., Bologna (IT)

(72) Inventors: Leopoldo Della Ciana, Bologna (IT); Lorenzo Biagini, Bologna (IT); Thomas Paul Jansen, Bologna (IT); Rossana Perciaccante, Bologna (IT); Manuela Vargiolu, Bologna (IT); Marina Eleonora Vettraino, Bologna (IT)

(73) Assignee: CYANAGEN S.r.l., Bologna (IT)

(*) Notice: Subject to any disclaimer, the term of this patent is extended or adjusted under 35 U.S.C. 154(b) by 160 days.

(21) Appl. No.: 17/156,027

(22) Filed: Jan. 22, 2021

(65) Prior Publication Data

US 2021/0231572 A1    Jul. 29, 2021

(30) Foreign Application Priority Data

Jan. 23, 2020  (IT) .......................... 102020000001327

(51) Int. Cl.
| | | |
|---|---|---|
| *G01N 21/76* | (2006.01) | |
| *C12Q 1/28* | (2006.01) | |
| *G01N 21/78* | (2006.01) | |
| *G01N 33/573* | (2006.01) | |
| *G01N 33/58* | (2006.01) | |

(52) U.S. Cl.
CPC .............. *G01N 21/76* (2013.01); *C12Q 1/28* (2013.01); *G01N 21/78* (2013.01); *G01N 33/573* (2013.01); *G01N 33/582* (2013.01); *G01N 2333/908* (2013.01); *G01N 2458/00* (2013.01)

(58) Field of Classification Search
CPC ...... G01N 21/76; G01N 21/78; G01N 33/573; G01N 33/582; G01N 2333/908; G01N 2458/00; C12Q 1/28; C09K 11/07; C09K 2211/1044; C09K 2211/1059
See application file for complete search history.

(56) References Cited

U.S. PATENT DOCUMENTS

2010/0273189 A1*  10/2010  Akhavan-Tafti ........ C09B 15/00
                                                            435/7.9
2016/0266045 A1      9/2016  Wang et al.

FOREIGN PATENT DOCUMENTS

| WO | 01/55446 | 8/2001 | |
|---|---|---|---|
| WO | 2008/081455 | 7/2008 | |
| WO | WO-2008081455 A2 * | 7/2008 | ............. B82Y 15/00 |
| WO | 2010/099486 | 9/2010 | |

OTHER PUBLICATIONS

Italian Search Report and Written Opinion for IT202000001327 dated Sep. 10, 2020, 7 pages.

* cited by examiner

*Primary Examiner* — Jennifer Wecker
*Assistant Examiner* — Alea N. Martin
(74) *Attorney, Agent, or Firm* — Nixon & Vanderhye P.C.

(57) ABSTRACT

A kit for performing an assay for determining an analyte in a sample with an extended shelf-life, wherein the kit comprises a chemiluminescent cyclic dihydrazide, an enhancer, a co-enhancer, and a peroxide oxidizer. The kit is useful in blot assays and immunoassays for the detection of proteins and nucleic acid molecules.

16 Claims, 9 Drawing Sheets luminol isoluminol

DML

DEL

L-012

SPOX

SBOX

CPOX

CBOX

L/SPOX 16     Amersham ECL Prime™

(a)

L/SPOX 2     Westar SUPERNOVA (b)

L012/SPOX     Supersignal™ West Femto (c)

CHEMILUMINESCENT SUBSTRATES FOR PEROXIDASE WITH EXTENDED SHELF-LIFE

This application claims priority to IT Patent Application No. 102020000001327 filed Jan. 23, 2020, the entire contents of each of which are hereby incorporated by reference.

FIELD OF THE INVENTION

The present invention concerns a chemiluminescent substrate for assaying peroxidases in an assay for determining an analyte in a sample, wherein the chemiluminescent substrate has an extended shelf-life.

BACKGROUND ART

The chemiluminescent oxidation of luminol catalyzed by horseradish peroxidase (HRP) finds wide employment in analytical tests of antigens, antibodies and nucleic acids, and, in particular, blotting tests, e.g. Dot and Western Blots (proteins), Southern and Northern Blots (nucleic acids), as well as in Enzyme Linked Immunoassays (EIA, for either protein or nucleic acids).

It is known that the chemiluminescent oxidation of luminol catalyzed by HRP can be made faster and more efficient by adding an electron mediator, or enhancer, as shown, for example, by Kricka L J (1991), *Clinical Chemistry*, 37:1472-1481; or by Kricka L J, Voyta J C and Bronstein I in "Chemiluminescent Methods for Detecting and Quantitating Enzyme Activity" (2000), *Methods Enzymol;* 305:370-390.

The mechanism of the enhanced chemiluminescence reaction (ECL), where luminol and an enhancer are oxidized simultaneously, has been described as follows [Lind J, Merenyi G, and Eriksen T E (1983), *J Am Chem Soc*, 105: 7655-7661]. In the first step of ECL, the enhancer (E), which is a more active substrate for HRP than luminol, is oxidized by hydrogen peroxide in the presence of HRP according to a "ping-pong" mechanism:

$$HRP + H_2O_2 \rightarrow HRP\text{-}I \quad (1)$$

$$HRP\text{-}I + E \rightarrow HRP\text{-}II + E. \quad (2)$$

$$HRP\text{-}II + E \rightarrow HRP + E. \quad (3)$$

where E is the enhancer, E. is a radical product of one-electron oxidation of the enhancer, HRP is the Horseradish Peroxidase enzyme in its Fe(III) resting state, HRP-I and HRP-II are the oxidized intermediates of the peroxidase, which are, by two and one oxidation equivalents, above the resting state, respectively. Then, the radical product of the enhancer (E.) reacts reversibly with a luminol molecule (LH$^-$) [Easton P M, Simmonds A C, Rakishev A, Egorov A M, and Candeias L P (1996), *J Am Chem Soc;* 6619-6624]:

$$E. + LH^- \leftrightharpoons E + L.^- \quad (4)$$

Thermodynamically, the position of redox equilibrium (4) is determined by the difference between the reduction potentials of the enhancer and luminol radicals under the conditions of the experiment. Once formed, two luminol radicals (L.$^-$) dismute to luminol anion (LH$^-$) and diazaquinone intermediate (L):

$$2L.^- \rightarrow LH^- + L \quad (5)$$

The diazaquinone intermediate (L) reacts with hydrogen peroxide with formation of a luminol peroxide (LO$_2^{2-}$), which collapses to the excited state of 3-aminophthalate ([AP$^{2-}$]*) with expulsion of molecular nitrogen; [AP$^{2-}$]* then returns to the ground state (AP$^{2-}$) with emission of a photon (hv) at 425 nm:

$$L + H_2O_2 \rightarrow LO_2^{2-} \rightarrow [AP^{2-}]^* + N_2 \rightarrow AP^{2-} + h\nu \quad (6)$$

The intensity of emitted light is proportional to the square of the rate of generation of luminol radicals (L.$^-$). The quadratic relation is a consequence of the mechanism of generation of the excited species, which involves the dismutation of two luminol radicals, Equation 5. In turn, the rate of generation of luminol radicals is given by the rate of enzyme turnover, weighted by the fraction of the radicals generated that results in luminol radicals (L.$^-$) after redox equilibrium (4). The rate of enzyme turnover is governed by the rate-determining step, the reduction of HRP-II to ferric enzyme (HRP), Equation (3). In conclusion, the enhancement of chemiluminescence can be described to a good approximation by considering (a) the acceleration of the enzyme turnover by reaction of the enhancer with HRP-II and (b) the reversible electron-transfer reaction between the enhancer radical and luminol.

A number of compounds were successfully used in the enhancement of HRP-induced chemiluminescence including luciferin, 6-hydroxybenzotriazols, p-iodophenols, p-coumaric acid and other phenolic enhancers (Thorpe G H G and Kricka L J (1986) *Methods Enzymol* 133:331); aromatic amines (U.S. Pat. No. 4,279,950); acetanilides (Eur. Pat. Appl. No. 603953); N-substituted phenothiazines (U.S. Pat. Nos. 5,171,688 and 6,432,662); boronic acids (U.S. Pat. No. 5,629,168).

A further, great increase in chemiluminescent light emission was obtained with certain 4-dialkylaminopyridines, such as 4-morpholino-pyridine (MORP), 4-dimethylamino-pyridine (DMAP) and 4-pyrrolidinopyridine (PPY), as described in U.S. Pat. No. 7,803,573. These compounds, belonging to the class of 4-aminopyridines, provide a further enhancement in light output only when used in conjunction with primary, electron transfer type, enhancers. Thus, they can been described as secondary enhancers, or co-enhancer, as in Vdovenko M M, Della Ciana L, and Sakharov I Y (2009) *Anal Biochem* 392:54. Addition of 4-dialkylamino-pyridines to a substrate solution containing the SPTZ enhancer significantly increased the rate of production of SPTZ cation radicals, equations (2) and (3), thus increasing HRP turnover as described in Sakharov I Y and Vdovenko M M (2013) *Anal Biochem* 434:12. Another group of compounds behaving as co-enhancers is described in U.S. Pat. No. 9,040,252. These co-enhancers belong to the class of N-azoles, the most useful being imidazole, 1-methyl-imidazole, 1,2,3-triazole and 1,2,4-triazole.

In practical operation, the user will mix two separate, previously prepared buffer solutions, one part containing the luminol and enhancers, the other part the peroxide oxidizer. While the two separate solutions can be stored for a long period of time, the resulting "Working Solution" obtained by mixing the two partial solutions has limited stability, ranging from a few hours, to, at most, several days.

Thus, it is desirable to eliminate the need to mix separate components at the time of the test procedure, without reducing or compromising the performance of the substrate.

Previous attempts at providing complete peroxidase substrates with extended storage stability have met very limited success. For example, Giri in U.S. Pat. No. 6,602,679 discloses formulations with extended stability, containing enhancers and peroxide stabilizers. However, no stability data are reported. Similarly, Woerner, in U.S. Pat. Appl. 2007/0264647, describes the use of stannous halides as stabilizers of hydrogen peroxide under alkaline conditions for use in chemiluminescent, fluorescent and colorimetric detection of peroxidase type assays. While it is claimed that, "by stabilizing and/or enhancing hydrogen peroxide in the buffer system, the compositions used in such assays may have a higher shelf life", no experimental evidence is given.

Thus, notwithstanding what has been previously reported, there is still a need for improved formulations of substrates for the enhanced chemiluminescent detection of peroxidase with all the components mixed in a buffer solution and with an extended shelf life.

OBJECT AND SUMMARY OF THE INVENTION

Object of the present invention is to provide a novel chemiluminescent substrate for quantitatively determining a peroxidase enzyme in assays for the detection of an analyte in a sample, wherein the chemiluminescent substrate has an extended shelf life. According to the invention, the above object is achieved thanks to the kits specified in the ensuing claims, which are understood as forming an integral part of the present description.

According to one embodiment, the present disclosure concerns a kit for performing an assay for determining an analyte in a sample, wherein the kit comprises a chemiluminescent cyclic diacylhydrazide, a peroxide oxidizer, an enhancer and a co-enhancer, wherein the enhancer is an anionic N-alkylphenoxazine and the co-enhancer is selected from a 4-dialkylaminopyridine and an N-azole.

According to a further embodiment, the present disclosure concerns a method for performing a chemiluminescent assay for detecting an analyte in a sample, wherein the method employs the kit herein disclosed.

BRIEF DESCRIPTION OF THE DRAWINGS

The invention will now be described, by way of example only, with reference to the enclosed figures of drawing, wherein.

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The present invention concerns a kit for performing an assay for determining an analyte in a sample, wherein the kit comprises a chemiluminescent diacyldihydrazide, a peroxide oxidizer, an enhancer and a co-enhancer, wherein the enhancer is an anionic N-alkylphenoxazine and the co-enhancer is selected from a 4-dialkylaminopyridine and an N-azole.

Figure 1:
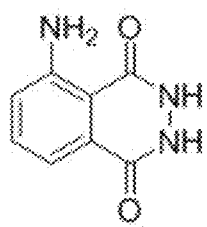
FIG. 1 shows the structures of cyclic diacylhydrazides of this invention.
Figure 1:
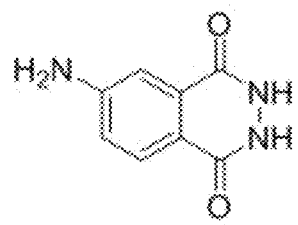
Figure 1:
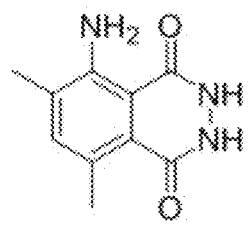
Figure 1:
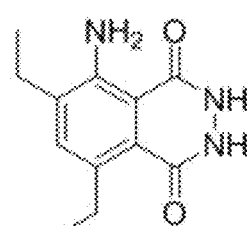
Figure 1:
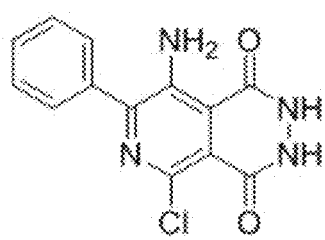

In an embodiment, the chemiluminescent diacyldihydrazide is selected from the group consisting of luminol, isoluminol, 5-amino-6,8-dimethyl-2,3-dihydrophthalazine-1,4-dione (DML), 5-amino-6,8-diethyl-2,3-dihydrophthalazine-1,4-dione (DEL), and 8-amino-5-chloro-7-phenylpyrido[3,4-d]pyridazine-1,4(2H,3H)-dione (L-012). The chemical structures of these chemiluminescent diacyldihydrazides are shown in FIG. 1. Preferably, the chemiluminescent diacyldihydrazide is selected from Luminol and 8-amino-5-chloro-7-phenylpyrido[3,4-d]pyridazine-1,4(2H,3H)-dione (L-012).

Figure 2:
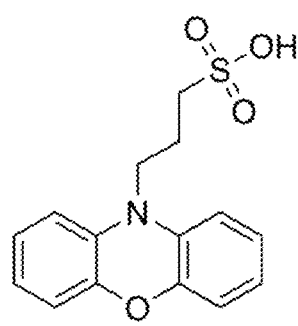
FIG. 2 shows the structures of anionic N-alkylphenoxazine enhancers of this invention.
Figure 2:
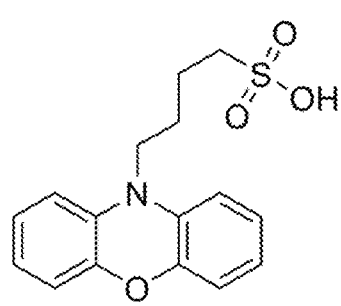
Figure 2:
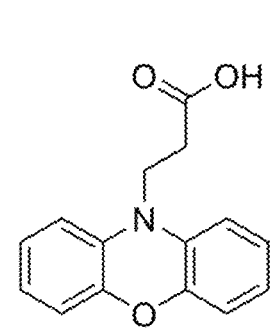
Figure 2:
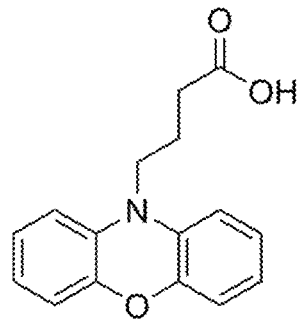

In an embodiment, the anionic N-alkylphenoxazine is selected from the group consisting of 3-(10H-phenoxazin-10-yl)propane-1-sulfonic acid (SPDX), 4-(10H-phenoxazin-10-yl)butane-1-sulfonic acid (SBOX), 3-(10H-phenoxazine-10-yl)propanoic acid (CPDX) and 4-(10H-phenoxazine-10-yl)butanoic acid (CBOX) and their salts. The chemical structures of these N-alkylphenoxazines are shown in FIG. 2. Preferably, the anionic N-alkylphenoxazine is selected from 3-(10H-phenoxazin-10-yl)propane-1-sulfonic acid (SPDX) and 3-(10H-phenoxazine-10-yl)propanoic acid (CPDX).

Co-enhancers of the present invention belong to two different classes of compounds, 4-dialkylaminopyridines (as described in U.S. Pat. No. 7,803,573), and N-azoles (as described in U.S. Pat. No. 9,040,252). Among 4-dialkylaminopyridines, preferred compounds are 4-morpholino-pyridine (MORP), 4-dimethylaminopyridine (DMAP) and 4-pyrrolidinopyridine (PPY). Among N-azoles, preferred compounds are imidazole and 1-methyl-imidazole.

The peroxide oxidizer according to the present invention may be hydrogen peroxide, or any complex of hydrogen peroxide, which—upon dissolution in aqueous solution—releases hydrogen peroxide, such as perborates, percarbonates or the urea/hydrogen peroxide complex in a molar ratio equal to 1:1. In a preferred embodiment, the peroxide oxidizer is selected among hydrogen peroxide, urea/hydrogen peroxide complex, a perborate salt, a percarbonate salt. Preferably, the perborate and percarbonate salts are alkaline or alkaline earth salts.

In a further embodiment, the kit further comprises a peroxidase enzyme.

The peroxidase enzyme is any peroxidase suitable for use in chemiluminescence assays. According to an embodiment, the peroxidase enzyme is selected among horseradish peroxidase (for example Sigma type VIA or IX), or an anionic peroxidase, like soybean peroxidase and sweet potato peroxidase.

The peroxidase enzyme can be either conjugated or not conjugated with a detection reagent for the analyte to be detected. The peroxidase enzyme (or the conjugate thereof) can be added by the final user.

The limited storage stability of enhanced chemiluminescent substrates for peroxidase is accountable to two main causes: (1) oxidation of the enhancer (2) decomposition of hydrogen peroxide. Of these two causes, the first, oxidation of the enhancer, is by far the most important. Other components of the substrate, such as cyclic diacylhydrazides, co-enhancers and buffer are essentially stable to oxidation by either molecular oxygen or peroxide, even in alkaline solution.

Oxidation of the enhancer can occur by reaction with molecular oxygen, or with peroxide. These oxidation reactions are generally faster as the pH increases, and are catalyzed by traces of metal ions, especially iron and copper.

Certain classes of enhancers, such as phenolic enhancers, are subject to fast oxidation even by molecular oxygen. In fact, solutions containing luminol and phenolic enhancers must be stored at 4° C., as they lose a large percentage of their activity if stored for even one day at room temperature.

Figure 3:
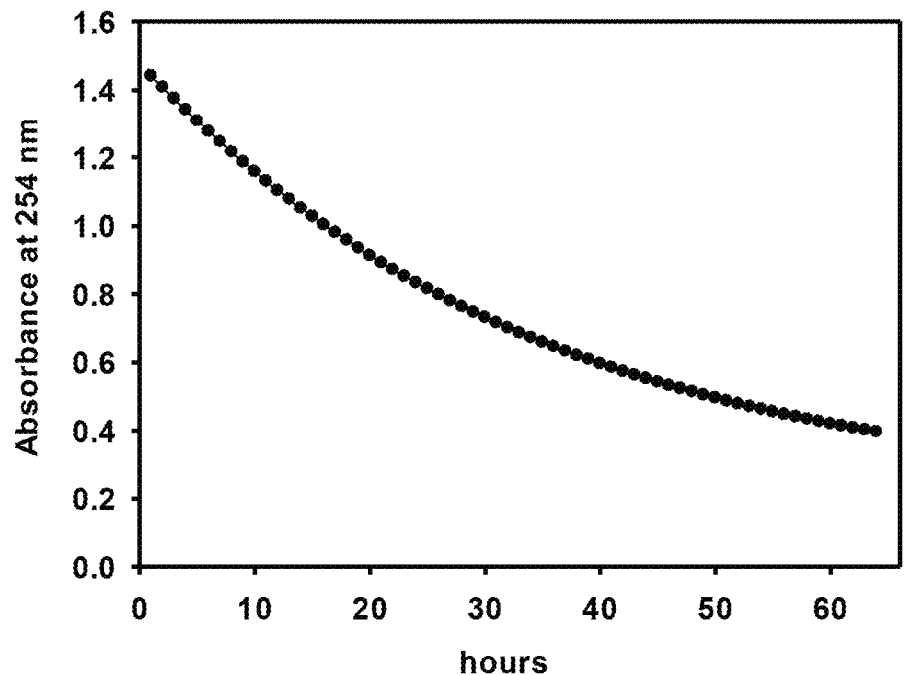
FIG. 3 shows a graph of the oxidation kinetics of SPTZ.

N-alkylphenothiazines enhancers, such as 3-(10'-phenothiazinyl) propane-1-sulfonate (SPTZ) are stable to oxidation by molecular oxygen for very long periods even in alkaline solutions kept at room temperature. However, they slowly decompose in the presence of peroxides (FIG. 3). The simultaneous decrease in concentration of both enhancer and peroxide leads to a degradation of performance.

Figure 4:
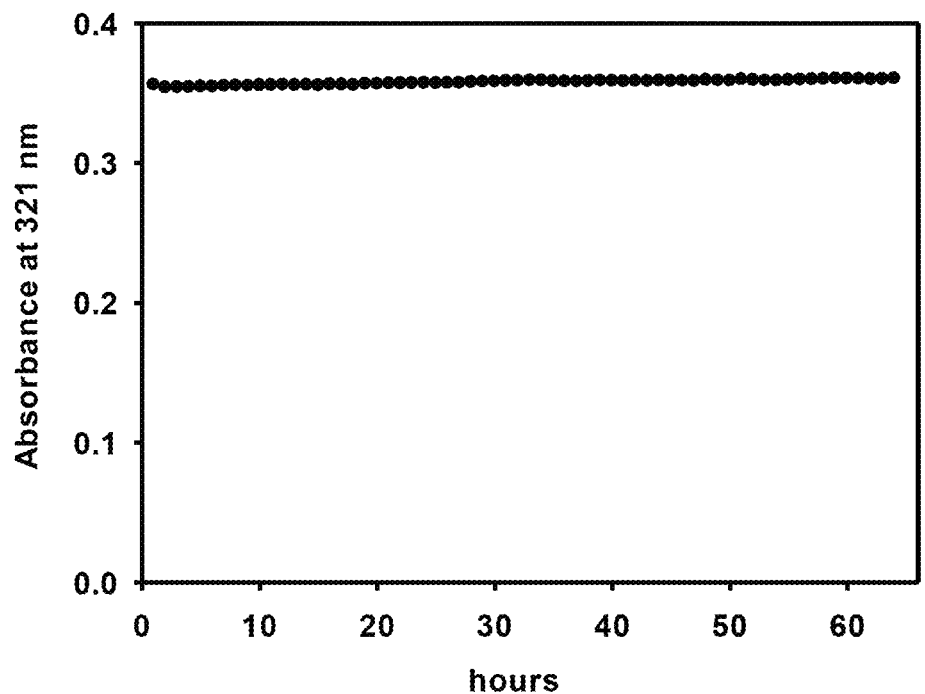
FIG. 4 shows a graph of the oxidation kinetics of SPDX.

In contrast, the present inventors found that anionic N-alkylphenoxazines enhancers are extremely stable to oxidation by peroxides, even in alkaline solutions (FIG. 4).

This finding strongly suggests that the main factor affecting the storage stability of enhanced chemiluminescence substrates is the stability toward oxidation of the enhancer itself. In contrast, Giri in U.S. Pat. No. 6,602,679 and Woerner, in U.S. Pat. Appl. 2007/0264647 rely exclusively on the addition of peroxide stabilizers to improve the storage stability of enhanced chemiluminescent substrates, neglecting the role of the enhancer.

On this basis, the present inventors developed chemiluminescent substrates in which anionic N-alkylphenothiazines were replaced, as enhancers, by anionic N-alkylphenoxazines, Examples 2-10. Optimized formulations of chemiluminescent substrates based on luminol or L-012, with 3-(10'-phenoxazinyl) propane-1-sulfonate (SPDX) as enhancer and MORP or imidazole as co-enhancer are disclosed in Example 11. The performance of these substrates is similar or superior to reference substrates with SPTZ as enhancer, L/SPTZ1 and L/SPTZ2 (Example 2), both in terms of initial chemiluminescent signal, FIG. 13, and Western Blotting immunoassays, FIGS. 14 (a), (b), (c).

Stability studies were carried out on the substrates of Example 11 both at 4° C. and 23° C. Initial chemiluminescent signals were recorded immediately after mixing all the components. Results are shown in Table I and FIG. 13 (4° C.), and Table II (23° C.). On both cases, substrates containing SPDX as enhancer are much more stable than those with SPTZ.

TABLE I

| | % Initial Signal Loss at 4° C. (days) | | |
|---|---|---|---|
| Substrate | 30 | 60 | 130 |
| L/SPTZ1 | 85 | 100 | 100 |
| L/SPTZ2 | 100 | 100 | 100 |
| L/SPOX2 | 0 | 0 | 25 |
| L/SPOX6 | 0 | 0 | 5 |
| L/SPOX10 | 0 | 5 | 10 |
| L/SPOX16 | 0 | 0 | 5 |
| L012/SPOX | 0 | 0 | 0 |

TABLE II

| | % Initial Signal Loss at 23° C. (days) | | |
|---|---|---|---|
| Substrate | 15 | 30 | 60 |
| L/SPTZ1 | 100 | 100 | 100 |
| L/SPTZ2 | 100 | 100 | 100 |
| L/SPOX2 | 10 | 20 | 30 |
| L/SPOX6 | 0 | 5 | 15 |
| L/SPOX10 | 0 | 5 | 15 |
| L/SPOX16 | 0 | 0 | 0 |
| L012/SPOX | 0 | 0 | 10 |

Figure 15:
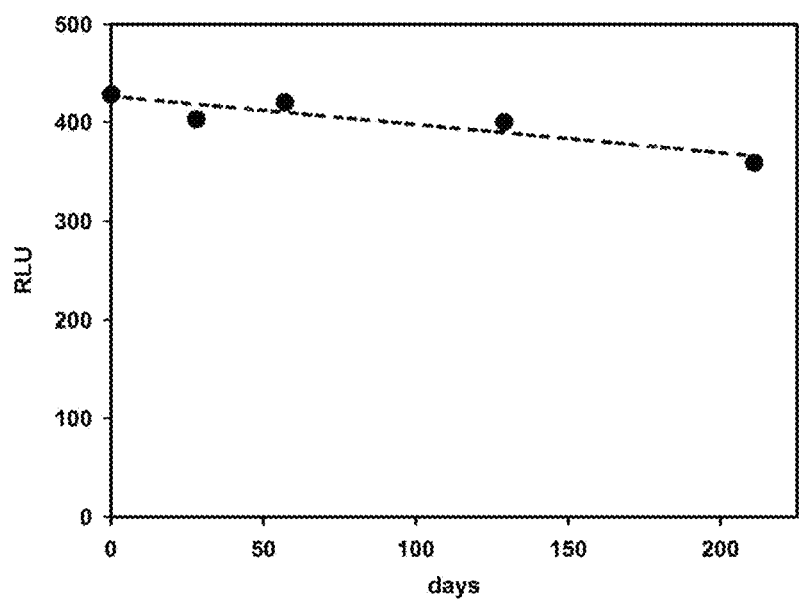
FIG. 15 shows a graph of the chemiluminescent signal of substrate L/SPDX6, prepared as described in Example 11, vs. time of storage at 4° C.
Figure 16:
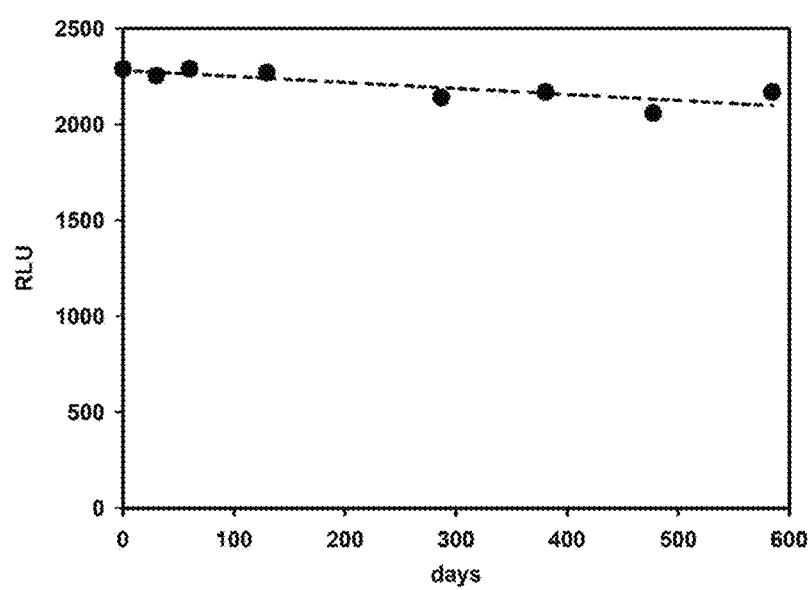
FIG. 16 shows a graph of the chemiluminescent signal of substrate L012/SPDX, prepared as described in Example 11, vs. time of storage at 4° C.

The most promising substrates were monitored for longer time periods. Results are summarized in FIG. 15 for L/SPXO6. This substrate shows a signal decrease of about 15% after storage at 4° C. for 211 days (7 months). Even better storage stability is found with L012/SPDX substrate, FIG. 16. In this case, a signal decrease of only 8% is observed, after storage at 4° C. for 585 days (almost 20 months).

In an embodiment, the kit comprises a chemiluminescent cyclic diacylhydrazide, a peroxide oxidizer, an enhancer and a co-enhancer, wherein the chemiluminescent cyclic diacyldihydrazide is present in a first vial and the peroxide oxidizer is present in a second vial, and wherein the enhancer and the co-enhancer are present either in the first vial or in the second vial or in both vials. The second vial containing the peroxide oxidizer is free of any stabilizer of the peroxide oxidizer. The kit reagents are present in the vials either in a liquid or solid state. If the kit reagents are in solid state, they can be present in powder or tablet form and have to be reconstituted in a liquid phase by addition of water or a buffering solution at the time of use. Enhancer(s) and co-enhancer(s), as well as other additives, such as chelators and stabilizers, can be added to either the chemiluminescent cyclic dihydrazide or peroxide oxidizer vials, or both, provided that the stabilizer(s) is (are) not stabilizer(s) of the peroxide oxidizer. The two vials can also contain buffering substances that upon mixing generate a chemiluminescent substrate, or "Working Solution", having a pH value suitable for performing the assay. The Working Solution obtained by mixing the above listed compounds is stable for a long period of time (generally 6 months or longer) and is free of any stabilizer of the peroxide oxidizer.

In an embodiment, the chemiluminescent cyclic diacyldihydrazide, the peroxide oxidizer, the enhancer, the co-enhancer are formulated in a single vial and in absence of any stabilizer of the peroxide oxidizer.

The peroxidase enzyme or a conjugate thereof—if present in the kit—is not stored together with its substrate component (i.e. the peroxide oxidizer), but in a different vial.

According to a further embodiment, the present disclosure concerns a method for performing a chemiluminescent assay for the detection of an analyte in a sample.

The term "assay" means the detection, semi-quantification and quantification of an analyte. Typically, the implementation of an assay requires to relate the light output to the amount of peroxidase used. The emission of light is thus detected or measured so that the presence and/or the amount of analyte is related to the production of light.

According to the present disclosure, the implementation of an assay requires to relate the light output generated by the chemiluminescente reaction of a chemiluminescent cyclic diacyldihydrazide reacted with a peroxidase enzyme, an enhancer, a co-enhancer and a peroxide oxidizer to the amount of any of the reaction partners (i.e. any one of chemiluminescent cyclic diacyldihydrazide, the peroxidase enzyme, the peroxide oxidizer, the enhancer, and the co-enhancer). According to a preferred embodiment, the light output is related to the amount of the peroxidase enzyme used.

The method for performing a chemiluminescent assay for the detection of an analyte in a sample comprises the following steps:

(i) realizing a chemiluminescent substrate by means of mixing together a chemiluminescent cyclic diacyldihydrazide, an enhancer, a co-enhancer and a peroxide oxidizer, wherein the enhancer is an anionic N-alkylphenoxazine and the co-enhancer is selected from a 4-dialkylaminopyridine and an N-azole, and wherein the chemiluminescent substrate is free of any stabilizer of the peroxide oxidizer, (ii) reacting a solid support, whereon the analyte of interest has been immobilized, with the chemiluminescent substrate, (iii) adding a detection reagent for the analyte of interest to the solid support, wherein the detection reagent is conjugated to a peroxidase enzyme, and (iv) recording the output light signal generated by the chemiluminescent reaction of the peroxidase enzyme with the chemiluminescent substrate, that correlates with the presence/amount of the analyte of interest.

In an embodiment, the chemiluminescent diacyldihydrazide is selected from the group consisting of luminol, isoluminol, 5-amino-6,8-dimethyl-2,3-dihydrophthalazine-1,4-dione (DML), 5-amino-6,8-diethyl-2,3-dihydrophthalazine-1,4-dione (DEL), and 8-amino-5-chloro-7-phenylpyrido[3,4-d]pyridazine-1,4(2H,3H)-dione (L-012). Preferably, the chemiluminescent diacyldihydrazide is selected from Luminol and 8-amino-5-chloro-7-phenylpyrido[3,4-d]pyridazine-1,4(2H,3H)-dione (L-012).

In an embodiment, the anionic N-alkylphenoxazine is selected from the group consisting of 3-(10H-phenoxazin-10-yl)propane-1-sulfonic acid (SPDX), 4-(10H-phenoxazin-10-yl)butane-1-sulfonic acid (SBOX), 3-(10H-phenoxazine-10-yl)propanoic acid (CPDX) and 4-(10H-phenoxazine-10-yl)butanoic acid (CBOX) and their salts.

Preferably, the anionic N-alkylphenoxazine is selected from 3-(10H-phenoxazin-10-yl)propane-1-sulfonic acid (SPDX) and 3-(10H-phenoxazine-10-yl)propanoic acid (CPDX).

Among 4-dialkylaminopyridines, preferred co-enhancers are 4-morpholino-pyridine (MORP), 4-dimethylaminopyridine (DMAP) and 4-pyrrolidinopyridine (PPY). Among N-azoles, preferred co-enhancers are imidazole and 1-methyl-imidazole.

The peroxide oxidizer according to the present invention may be hydrogen peroxide, or any complex of hydrogen peroxide, which—upon dissolution in aqueous solution—releases hydrogen peroxide, such as perborates, percarbonates or the urea/hydrogen peroxide complex in a molar ratio equal to 1:1. In a preferred embodiment, the peroxide oxidizer is selected among hydrogen peroxide, urea/hydrogen peroxide complex, a perborate salt, a percarbonate salt. Preferably, the perborate and percarbonate salts are alkaline or alkaline earth salts.

The peroxidase enzyme is any peroxidase suitable for use in chemiluminescence assays. According to an embodiment, the peroxidase enzyme is selected among horseradish peroxidase (for example Sigma type VIA or IX), or an anionic peroxidase, like soybean peroxidase and sweet potato peroxidase.

According to an embodiment, the concentration of the chemiluminescent cyclic diacyldihydrazide in the chemiluminescent substrate is comprised between 0.01 mM and 10 mM, preferably between 0.05 and 5.0 mM.

According to an embodiment, the concentration of the anionic N-alkylphenoxazine enhancer in the chemiluminescent substrate is comprised between 0.01 and 3 mM, preferably between 0.03 and 1.0 mM.

According to an embodiment, the concentration of the co-enhancer in the chemiluminescent substrate is comprised between 0.05 and 25 mM, preferably between 0.1 and 12 mM.

According to an embodiment, the concentration of the peroxide in the chemiluminescent substrate is comprised between 0.1 and 8 mM, preferably between 0.25 and 4 mM.

According to an embodiment, the pH of the chemiluminescent substrate is comprised between 6.0 and 9.5, preferably between 6.5 and 9.0.

According to a preferred embodiment, the chemiluminescent substrate (free of any stabilizer of peroxide oxidizer), having a pH comprised between 6.0 and 9.5, preferably between 6.5 and 9.0, contains:
  i) the chemiluminescent cyclic diacyldihydrazide in a concentration between 0.01 mM and 10 mM, preferably between 0.05 and 5 mM;
  ii) the anionic N-alkylphenoxazine enhancer in a concentration between 0.01 and 3 mM, preferably between 0.03 and 1 mM;
  iii) the co-enhancer in a concentration between 0.05 and 25 mM, preferably between 0.1 and 12 mM; and
  iv) the peroxide oxidizer in a concentration between 0.1 and 8 mM, preferably between 0.25 and 4.0 mM.

In performing the assay for detecting the analyte of interest (either in a qualitative or in a quantitative manner), the peroxidase enzyme is in the form of a conjugate with a detection reagent for the analyte to be detected. The detection reagent can be selected from a protein, an antibody, a nucleotide, an oligonucleotide or a nucleic acid molecule according to what kind of analyte is to be detected. The detection reagent conjugated to the peroxidase enzyme can be either (a) a detection reagent able to specifically bind the analyte or (b) a secondary detection reagent able to bind the detection reagent that specifically bind the analyte. In the latter case, the detection reagent that specifically bind the analyte is added to the chemiluminescent substrate or to the solid support, whereon the analyte of interest has been immobilized, and the secondary detection reagent able to bind the detection reagent is subsequently added to the solid support.

The chemiluminescent reactions of this invention are applicable to the detection and quantification of analytes, using, for example, the formation of a bond between the analyte (e.g. a protein or a nucleic acid molecule) and a solid support (e.g. a membrane or a microtiter plate) and using the peroxidase enzyme as tracer. The luminescent reaction is initiated by adding the chemiluminescent substrate as herein disclosed to the solid support (previously reacted with the analyte containing sample) and subsequently adding the peroxidase enzyme containing solution to the solid support. The emission of light is prolonged and can be measured by film, camera or other instrumentation.

Chemiluminescent assays based on the chemiluminescent substrate according to the present disclosure include dot blot and Western blot assays for proteins and Southern and Northern Blots assays for nucleic acids.

The blot assays based on the chemiluminescent substrate according to the present disclosure use gel electrophoresis to separate the analyte of interest (a protein or a nucleic acid molecule) from the other components (other proteins or other nucleic acid molecules) present in the sample to be tested. The analyte and the other components are then transferred to a membrane, where they are probed (detected) using the chemiluminescent substrate as disclosed herein and a detection reagent able to bind specifically the analyte of interest, wherein the detection reagent is conjugated to the peroxidase enzyme.

Chemiluminescent assays based on the chemiluminescent substrate of this invention also include enzyme immunoassays (EIA), like for example ELISA assays. Enzyme immunoassays are especially useful for detecting analytes present in the sample in extremely small quantities, such as tumor markers, thyroid hormones, virus proteins (e.g. HIV, HCV, HPV proteins), or steroid hormones (e.g. estradiol, aldosterone). Performing an ELISA assay for detecting an analyte involves at least one detection reagent with specificity for the analyte of interest. The analyte within the sample is immobilized on a solid support (usually a polystyrene microtiter plate) either non-specifically (via adsorption to the solid support surface) or specifically (via capture by another detection reagent specific to the same analyte to the solid support surface, in a "sandwich ELISA"). After the analyte is immobilized onto the solid support surface, the detection reagent is added, forming a complex with the analyte. The detection reagent can be covalently linked to a peroxidase enzyme as tracer, or can itself be detected by a secondary detecting reagent that is linked to a peroxidase enzyme through (bio)conjugation (like for example via biotin or streptavidin). Between each step, the plate is typically washed with a mild detergent solution to remove any proteins or antibodies that are not specifically bound. After the final wash step, the plate is developed by adding the chemiluminescent substrate herein described and—in the case the detection reagent is not directly conjugated to the peroxidase enzyme—the solution containing the peroxidase enzyme conjugated to the secondary detection reagent to produce a light signal, which indicates the quantity of analyte in the sample.

The following examples serve to illustrate specific aspects of the invention. However, they are not intended to limit the invention.

EXAMPLES

All the reagents used within the present application were purchased from Sigma-Aldrich, TCI Europe and Panreac.

5-amino-6,8-dimethyl-2,3-dihydrophthalazine-1,4-dione (DML) and 5-amino-6,8-diethyl-2,3-dihydrophthalazine-1, 4-dione (DEL) were synthesized according to Neumann H, Klaus S, Klawonn M, Struebing D, Huebner S, Goerdes D, von Wangelin A J, Lalk M and Beller M (2004) *Zeitschrift für Naturforschung B*, 59:431-438.

SPDX and CPDX enhancers were synthesized according to Kulvs J, Vidziunaite R, Janciene R, and Palaima A (2006) *Electroanalysis* 18:1771-1777.

Spectrophotometric measurements were carried out on a UV-VIS Varian—Cary 100 BIO. Chemiluminescent measurements were performed with a microplate, multilabel spectrometer, Victor$^3$ (Perkin-Elmer) on luminescence mode (no emission filter). Black 96 wells microplates were used, (Optiplate-96F).

HRP test solution was prepared diluting 15 µL of horseradish peroxidase (HRP) stock solution (20 mg/L) to 50 mL with buffer (concentration: 6 ng/mL). 28 µL of HRP were added to each well (228 µL final in-well volume). Thus, the HRP final amount in each well is 168 pg.

Example 1—Kinetics of Oxidation of SPTZ and SPDX by Sodium Perborate

The following solutions were prepared:
SPTZ Solution
[SPTZ]=0.05 mM
[sodium perborate]=4 mM
in 300 mM Tris buffer, pH 8.73
SPDX solution
[SPDX]=0.05 mM
[sodium perborate]=4 mM
in 300 mM Tris buffer, pH 8.73

2 mL aliquots of either solution were added to a 1 cm quartz cuvette. The cuvette was inserted in a thermostated cuvette holder kept at 35° C. Oxidation kinetics were monitored spectrophotometrically at 254 nm (SPTZ) and 312 nm (SPDX) for 64 h. Results are shown in FIG. 3 (SPTZ Solution) and FIG. 4 (SPDX Solution).

Example 2—Reference Chemiluminescent Substrates

Two chemiluminescent reference substrates were prepared as follows:
L/SPTZ1 substrate
[luminol]=5.0 mM
[sodium perborate]=4 mM
[SPTZ]=1.5 mM
in 150 mM Tris Buffer, pH 9.0.
Initial Signal is set at 100 RLU (relative light units)
L/SPTZ2 substrate
[luminol]=5.0 mM
[sodium perborate]=4.0 mM
[SPTZ]=3.0 mM
[MORP]=3.0 mM
in 125 mM Tris Buffer, pH 9.0.

The Initial Signal of L/SPTZ2 is 10 times higher than L/SPTZ1.

Figure 5:
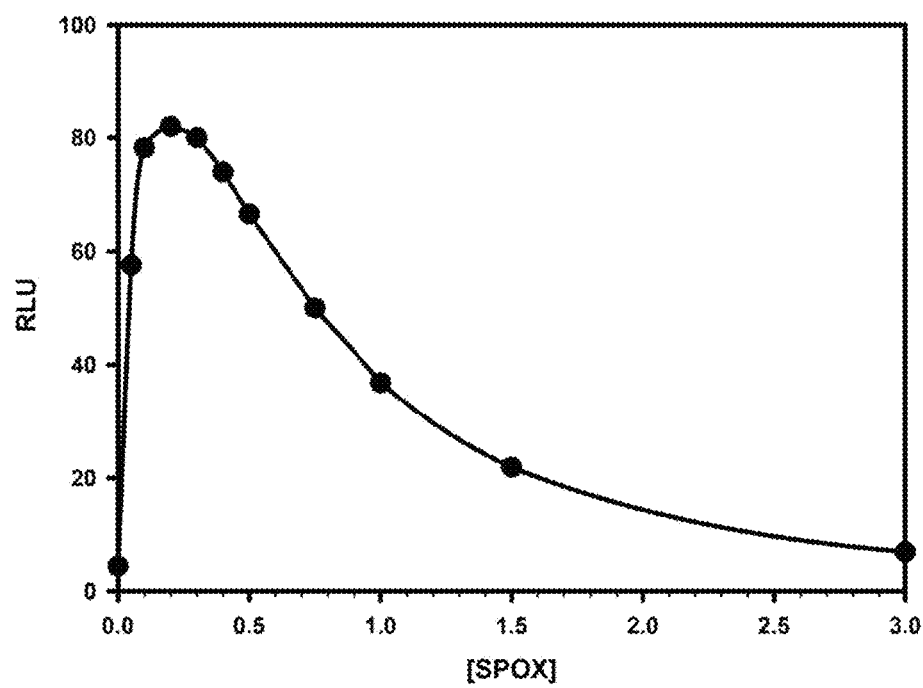
FIG. 5 shows the dependence of the chemiluminescent signal on SPDX concentration in a luminol/perborate/SPDX substrate.

Example 3—Dependence of the Chemiluminescent Signal on the Concentration of SPDX in Luminol/Perborate/SPDX/Substrates A series of chemiluminescent substrates was prepared with the following composition:
[luminol]=5.0 mM
[sodium perborate]=4 mM
[SPDX]=0-3.0 mM [enhancer]
in 125 mM Tris buffer, pH 9.0
200 µL of these substrates were placed in a black 96-wll-microplate. 30 µL of HRP solution (1/3700 of 20 mg/L solution) were added to each well and the plate was then placed in a Wallac Victor-3 plate reader.
Initial chemiluminescent signals, normalized with reference substrate L/SPTZ1 (Example 2) set at 100 RLU, are plotted vs. concentration of SPDX, as shown in FIG. 5.

Figure 6:
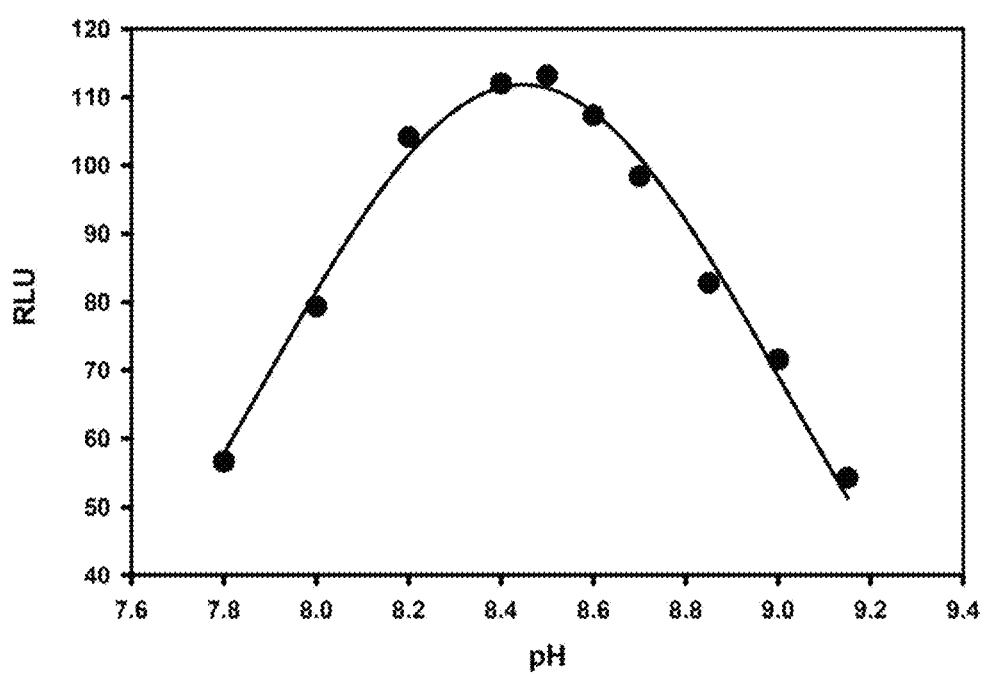
FIG. 6 shows the pH dependence of the chemiluminescent signal in a luminol/perborate/SPDX substrate.

Example 4—pH Dependence of the Chemiluminescent Signal in Luminol/Perborate/SPDX/Substrates A series of chemiluminescent substrates was prepared with the following composition:
[luminol]=5.0 mM
[sodium perborate]=4.0 mM
[SPDX]=0.3 mM (enhancer)
pH 7.80-9.30 125 mM Tris buffer
200 µL of these substrates were placed in a black 96-wll-microplate. 30 µL of HRP solution (1/3700 of 20 mg/L solution) were added to each well and the plate was then placed in a Wallac Victor-3 plate reader.
Initial chemiluminescent signals, normalized with reference substrate L/SPTZ1 (Example 2) set at 100 RLU, are plotted vs. pH, as shown in FIG. 6.

Figure 7:
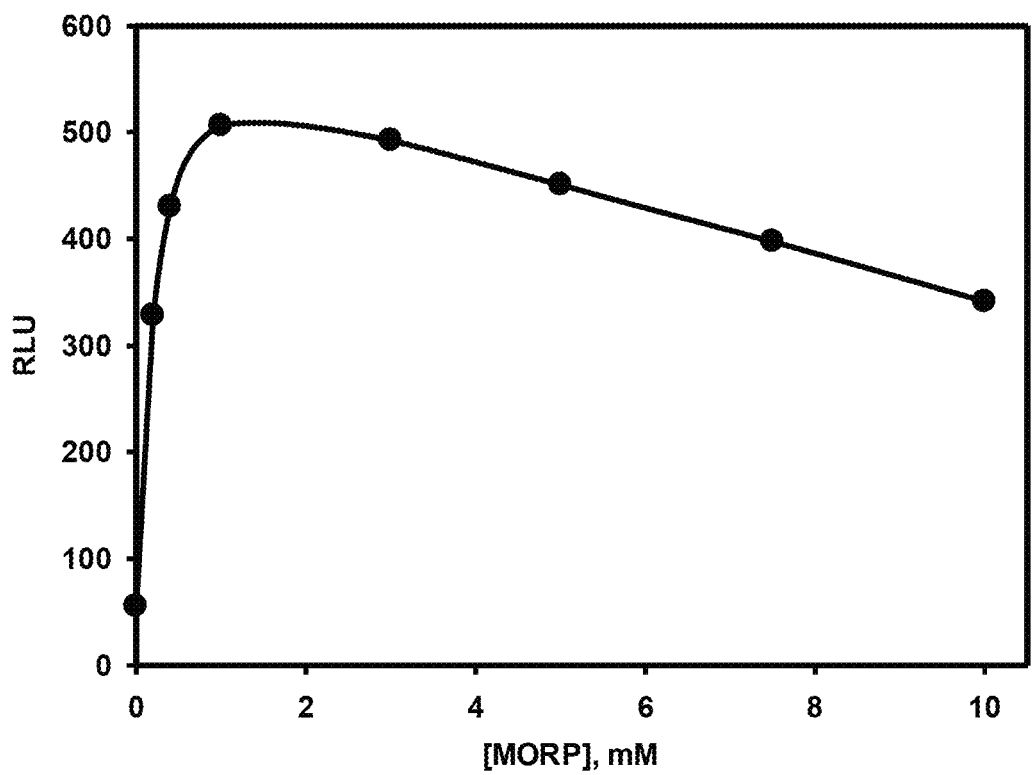
FIG. 7 shows the dependence of the chemiluminescent signal on MORP concentration in a luminol/perborate/SPDX/MORP substrate.

Example 5—Dependence of the Chemiluminescent Signal on the Concentration of MORP in Luminol/Perborate/SPDX/MORP Substrates A series of chemiluminescent substrates was prepared with the following composition:
[luminol]=5.0 mM
[sodium perborate]=4.0 mM
[SPDX]=3.0 mM (enhancer)
[MORP]=0-10 mM (co-enhancer)
in pH 9.0, 125 mM Tris Buffer
200 µL of these substrates were placed in a black 96-wll-microplate. 30 µL of HRP solution (1/3700 of 20 mg/L solution) were added to each well and the plate was then placed in a Wallac Victor-3 plate reader.
Initial chemiluminescent signals, normalized with reference substrate L/SPTZ1 (Example 2) set at 100 RLU, are plotted vs. concentration of MORP, as shown in FIG. 7.

Figure 8:
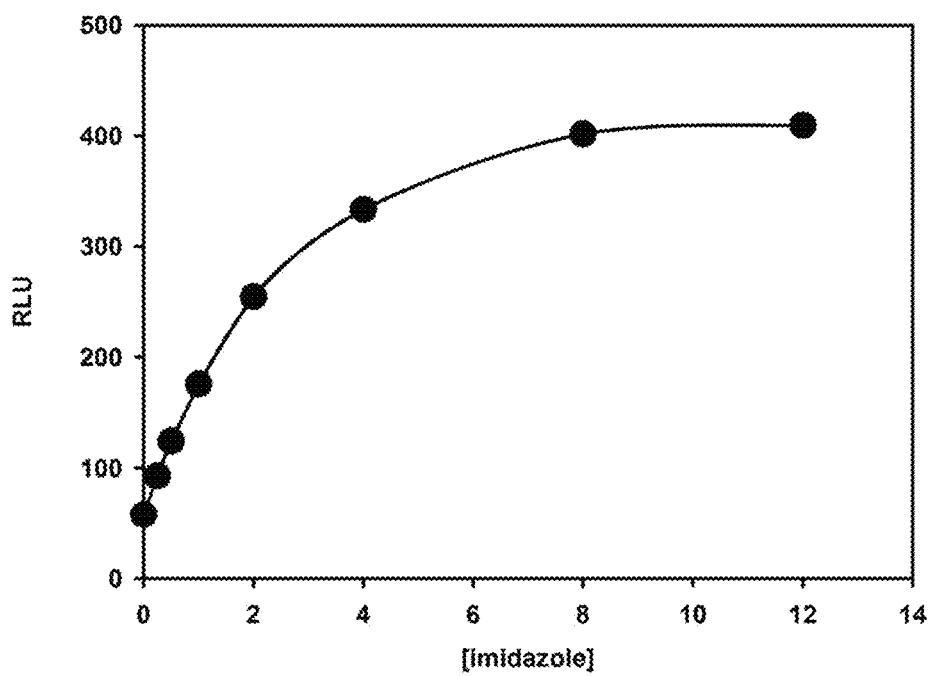
FIG. 8 shows the dependence of the chemiluminescent signal on imidazole concentration in a luminol/perborate/SPDX/imidazole substrate.

Example 6—Dependence of the Chemiluminescent Signal on the Concentration of Imidazole in Luminol/Perborate/SPDX/Imidazole Substrates A series of chemiluminescent substrates was prepared with the following composition:
[luminol]=0.15 mM
[sodium perborate]=4.0 mM
[SPDX]=0.3 mM (enhancer)
[imidazole]=0-20 mM (co-enhancer)
in pH 9.0, 125 mM Tris Buffer
200 µL of these substrates were placed in a black 96-well-microplate. 30 µL of HRP solution (1/3700 of 20 mg/L solution) were added to each well and the plate was then placed in a Wallac Victor-3 plate reader.
Initial chemiluminescent signals, normalized with reference substrate L/SPTZ1 (Example 2) set at 100 RLU, are plotted vs. concentration of imidazole, as shown in FIG. 8.

Figure 9:
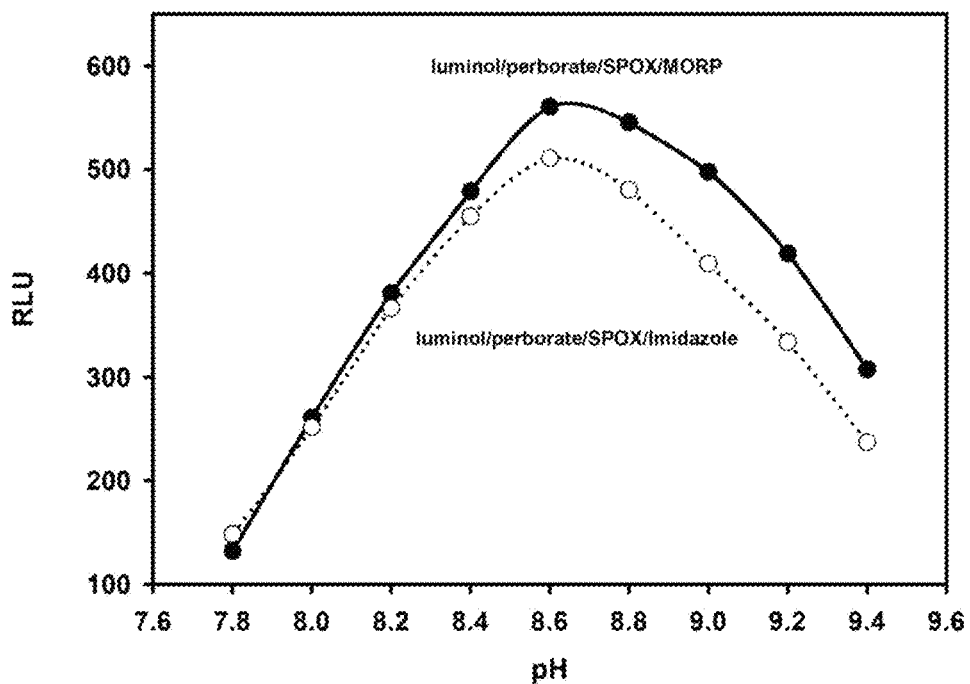
FIG. 9 shows the pH dependence of the chemiluminescent signal in luminol/perborate/SPDX/MORP and luminol/perborate/SPDX/imidazole substrates.

Example 7—pH Dependence of the Chemiluminescent Signal in Luminol/Perborate/SPDX/MORP and Luminol/Perborate/SPDX/Imidazole Substrates Two series of chemiluminescent substrates was prepared with the following compositions:
co-enhancer=MORP
[luminol]=5.0 mM
[sodium perborate]=4.0 mM
[SPDX]=0.3 mM (enhancer)
[MORP]=3.0 mM (co-enhancer)
pH 7.80-9.40 125 mM Tris buffer
co-enhancer=imidazole
[luminol]=5.0 mM
[sodium perborate]=4.0 mM
[SPDX]=0.3 mM (enhancer)
[imidazole]=8.0 mM (co-enhancer)
pH 7.80-9.40 125 mM Tris buffer
200 µL of these substrates were placed in a black 96-wll-microplate. 30 µL of HRP solution (1/3700 of 20 mg/L solution) were added to each well and the plate was then placed in a Wallac Victor-3 plate reader.
Initial chemiluminescent signals, normalized with reference substrate L/SPTZ1 (Example 2) set at 100 RLU, are plotted vs. pH, as shown in FIG. 9.

Figure 10:
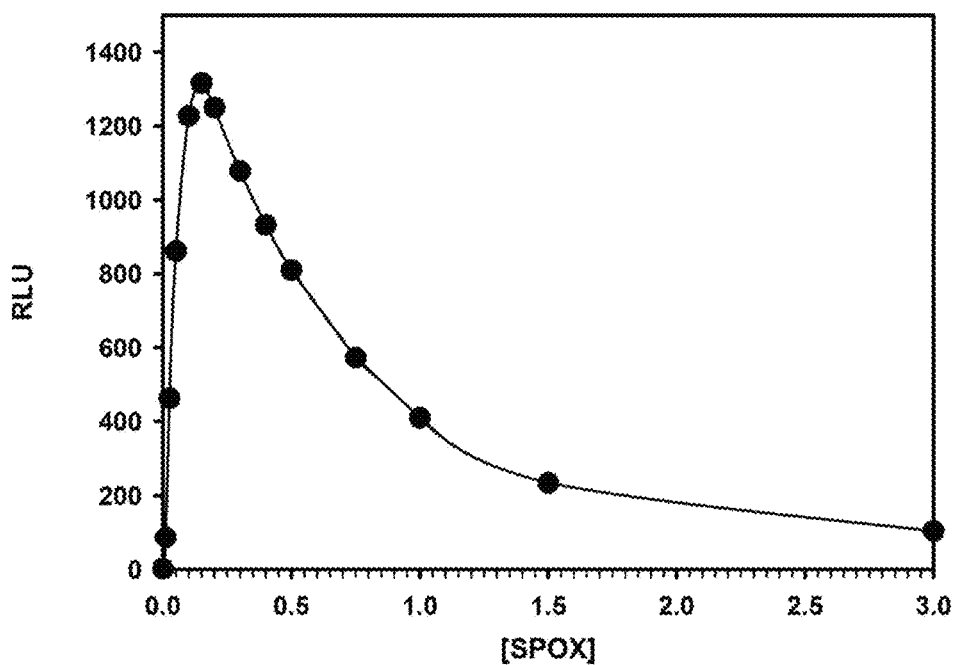
FIG. 10 shows the dependence of the chemiluminescent signal on SPDX concentration in an L-012/perborate/SPDX substrate.

Example 8—Dependence of the Chemiluminescent Signal on the Concentration of SPDX in L-012/Perborate/SPDX/Substrates A series of chemiluminescent substrates was prepared with the following composition:
[L-012]=0.15 mM
[sodium perborate]=4.0 mM
[SPDX]=0-0.4 mM (enhancer)
in pH 6.9, 125 mM Tris Buffer
200 µL of these substrates were placed in a black 96-wll-microplate. 30 µL of HRP solution (1/3700 of 20 mg/L solution) were added to each well and the plate was then placed in a Wallac Victor-3 plate reader.
Initial chemiluminescent signals, normalized with reference substrate L/SPTZ1 (Example 2) set at 100 RLU, are plotted vs. concentration of imidazole, as shown in FIG. 10.

Example 9—pH Dependence of the Chemiluminescent Signal in L-012/Perborate/SPDX/Substrates A series of chemiluminescent substrates was prepared with the following composition:
[L-012]=0.15 mM
[sodium perborate]=4.0 mM
[SPDX]=0.3 mM (enhancer)
pH 6.30-7.60 125 mM Tris buffer
200 µL of these substrates were placed in a black 96-wll-microplate. 30 µL of HRP solution (1/3700 of 20 mg/L solution) were added to each well and the plate was then placed in a Wallac Victor-3 plate reader.

Figure 11:
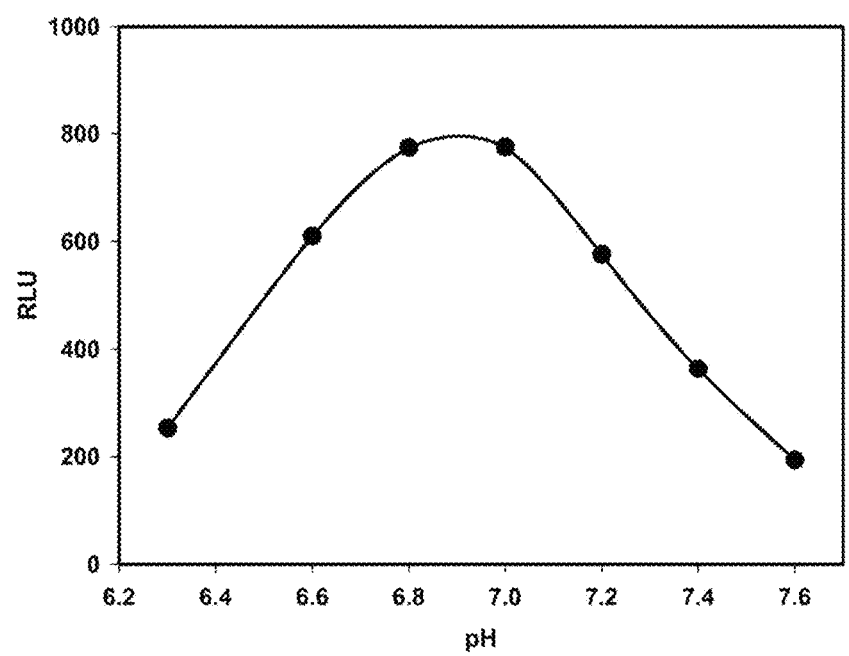
FIG. 11 shows the pH dependence of the chemiluminescent signal in an L-012/perborate/SPDX substrate.

Initial chemiluminescent signals, normalized with reference substrate L/SPTZ1 (Example 2) set at 100 RLU, are plotted vs. pH, as shown in FIG. 11.

Figure 12:
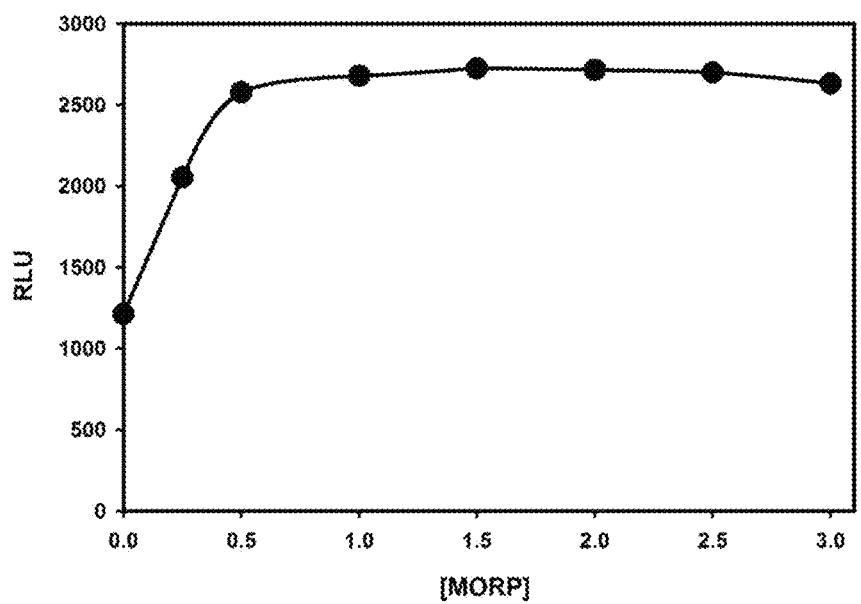
FIG. 12 shows the dependence of the chemiluminescent signal on MORP concentration in the L-012/perborate/SPDX/MORP substrate.

Example 10—Dependence of the Chemiluminescent Signal on the Concentration of MORP in L-012/Perborate/SPDX/MORP Substrates A series of chemiluminescent substrates was prepared with the following composition:
[L-012]=0.15 mM
[sodium perborate]=4.0 mM
[SPDX]=0.15 mM (enhancer)
[MORP]=0-3.0 mM
pH 6.9, 125 mM Tris Buffer 200 μL of these substrates were placed in a black 96-wll-microplate. 30 μL of HRP solution (1/3700 of 20 mg/L solution) were added to each well and the plate was then placed in a Wallac Victor-3 plate reader. Initial chemiluminescent signals, normalized with reference substrate L/SPTZ1 (Example 2) set at 100 RLU, are plotted vs. concentration of imidazole, as shown in FIG. 12.

Example 11—Luminol/SPDX and L-012/SPDX Vs. Luminol/SPTZ Substrates

Figure 13:
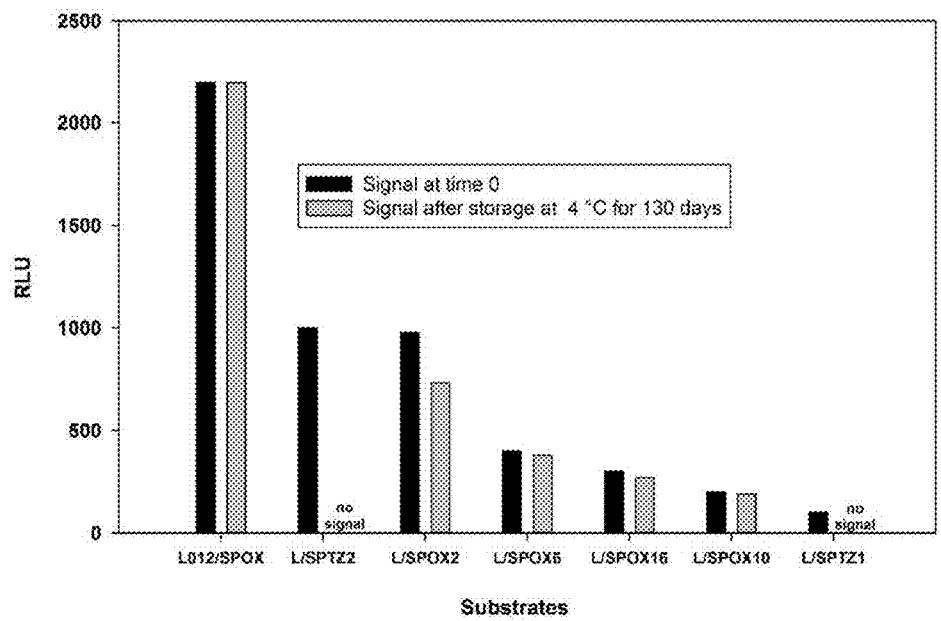
FIG. 13 shows Western Blots of Human IKBα obtained with luminol/SPDX and L-012/SPDX substrates vs. luminol/SPTZ substrates.

Three chemiluminescent substrates based on luminol with SPDX as enhancer were prepared as follows:
  1. L/SPDX2
[luminol]=4.0 mM
[sodium perborate]=4.0 mM
[SPDX]=1.0 mM (enhancer)
[MORP]=5.0 mM (co-enhancer)
in pH 9.00, 150 mM Tris buffer
co-enhancer=imidazole
  2. L/SPDX6
[luminol]=3.8 mM
[sodium perborate]=1.6 mM
[SPDX]=0.34 mM (enhancer)
[imidazole]=12.0 mM (co-enhancer)
in pH 9.00, 150 mM Tris buffer
  3. L/SPDX10
[luminol]=3.8 mM
[sodium perborate]=1.6 mM
[SPDX]=0.34 mM (enhancer)
[imidazole]=12.0 mM (co-enhancer)
in pH 8.20, 150 mM Tris buffer
  4. L/SPDX16
[luminol]=1.6 mM
[sodium perborate]=1.6 mM
[SPDX]=0.34 mM (enhancer)
[imidazole]=12.0 mM (co-enhancer)
in pH 8.85, 1M phosphate/diphosphate buffer
  5. L012/SPDX
[L-012]=0.6 mM
[sodium perborate]=1.75 mM
[SPDX]=0.74 mM (enhancer)
[MORP]=1.75 mM (co-enhancer)
in pH 7.6 50 mM/30 mM Tris/diphosphate buffer Initial chemiluminescent signal levels were recorded for each of these substrate, as well as the luminol/SPTZ reference substrates of example 2, L/SPTZ1 and L/SPTZ2. Results were plotted as a bar graph, as shown in FIG. 13.

Figure 14:
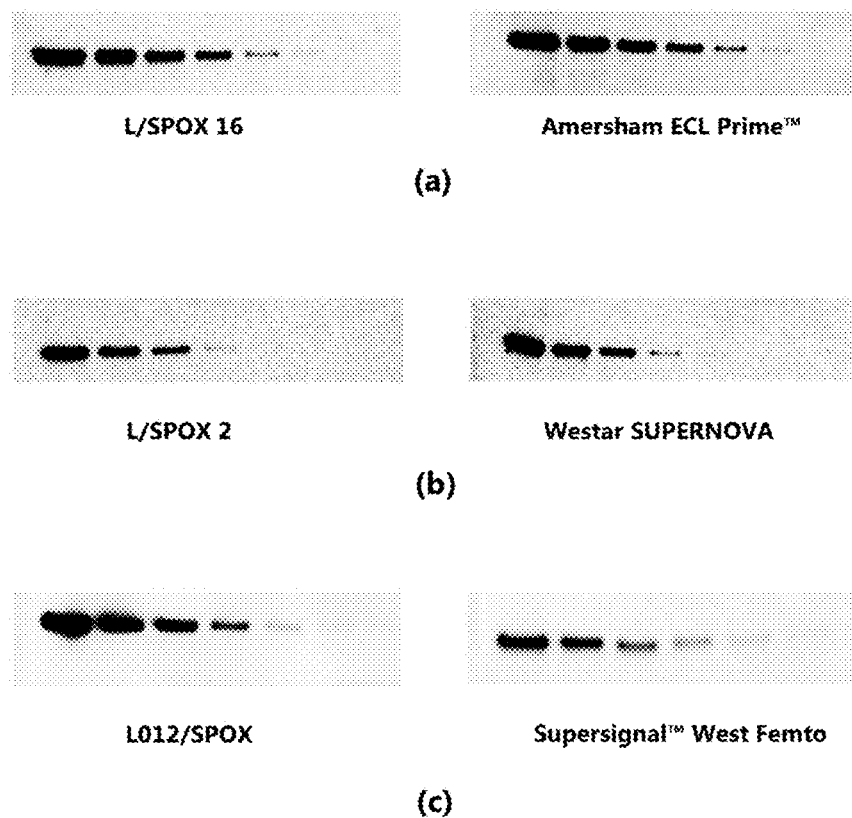
FIG. 14 shows Western Blots of Human IKBα obtained with luminol/SPDX and L-012/SPDX substrates vs. luminol/SPTZ substrates.

Example 12—Performance Comparisons Between Luminol/SPDX, L-012/SPDX Vs. Luminol/SPTZ Chemiluminescent Substrates in Western Blot Assays A series of luminol/SPDX chemiluminescent substrates was compared to that luminol/SPTZ substrates. The substrates were tested in western blotting to detect HDAC-1 in HeLa cell lysates. A serial of 2-fold dilutions of the cell lysate (from 5 to 0.078 μg)/(from 2.5 to 0.039 μg) was run on a 4-20% mini-PROTEAN TGX precast gel and blotted onto a nitrocellulose membrane with Trans-Blot® Turbo™ Transfer System. The membrane was blocked with 2% ECL™ Blocking Agent (GE Healthcare), probed with anti-HDAC-1 rabbit polyclonal antibody (Cat. No. ab19845, Abcam), and incubated with a secondary goat anti-rabbit HRP conjugated antibody (Cat. No. ab6721, Abcam). Chemiluminescent substrates were incubated with the blots for 1 minute and 30 seconds at room temperature prior to imaging with ImageQuant™ LAS 4000 (GE Healthcare). Images were taken at time 120 and 180 seconds. Results are shown in FIGS. 14 (a), (b), (c).

Naturally, while the principle of the invention remains the same, the details of construction and the embodiments may vary widely with respect to what has been described and illustrated by way of example, without departing from the scope of the present invention.

The invention claimed is:

1. Kit for performing an assay for determining an analyte in a sample, wherein the kit comprises a chemiluminescent cyclic diacylhydrazide, a peroxide oxidizer, an enhancer and a co-enhancer, wherein the enhancer is an anionic N-alkylphenoxazine and the co-enhancer is selected from a 4-dialkylaminopyridine or an N-azole.

2. Kit according to claim 1, wherein the kit further comprises a peroxidase enzyme or a conjugate thereof.

3. Kit according to claim 1, wherein the chemiluminescent cyclic diacyldihydrazide is selected from the group consisting of luminol, isoluminol, 5-amino-6,8-dimethyl-2,3-dihydrophthalazine-1,4-dione, 5-amino-6,8-diethyl-2,3-dihydrophthalazine-1,4-dione and 8-amino-5-chloro-7-phenylpyrido[3,4-d]pyridazine-1,4(2H,3H)-dione.

4. Kit according to claim 1, wherein the anionic N-alkylphenoxazine enhancer is selected from the group consisting of 3-(10H-phenoxazin-10-yl)propane-1-sulfonic acid, 4-(10H-phenoxazin-10-yl)butane-1-sulfonic acid, 3-(10H-phenoxazin-10-yl)propanoic acid and 4-(10H-phenoxazine-10-yl)butanoic acid, and their salts.

5. Kit according to claim 1, wherein the co-enhancer is selected among imidazole, 1-methylimidazole, 4-morpholinopyridine (MORP), 4-dimethylaminopyridine (DMAP) and 4-pyrrolidinopyridine (PPY).

6. Kit according to claim 1, wherein the peroxidase enzyme is selected among horseradish peroxidase, soybean peroxidase and sweet potato peroxidase.

7. Kit according to claim 1, wherein the peroxide oxidizer is selected among hydrogen peroxide, urea/hydrogen peroxide complex, a perborate salt, a percarbonate salt.

8. Kit according to claim 1, wherein the chemiluminescent cyclic diacyldihydrazide is present in a first vial and the peroxide oxidizer is present in a second vial, and wherein the enhancer and the co-enhancer are present either in the first vial or in the second vial or in both vials.

9. Kit according to claim 1, wherein the chemiluminescent cyclic diacyldihydrazide, the peroxide oxidizer, the enhancer and the co-enhancer are all present in a single vial.

10. A method for performing a chemiluminescent assay for the detection of an analyte in a sample, wherein the method comprises the following steps:
  (i) realizing a chemiluminescent substrate by means of mixing together a chemiluminescent cyclic diacyldihydrazide, an enhancer, a co-enhancer and a peroxide oxidizer, wherein the enhancer is an anionic N-alkylphenoxazine and the co-enhancer is selected from a 4-dialkylaminopyridine and an N-azole, and wherein the chemiluminescent substrate is free of any stabilizer of the peroxide oxidizer,
  (ii) reacting a solid support, whereon the analyte of interest has been immobilized, with the chemiluminescent substrate,
  (iii) adding a detection reagent for the analyte of interest to the solid support, wherein the detection reagent is directly or indirectly conjugated to a peroxidase enzyme, and
  (iv) recording the output light signal generated by the chemiluminescent reaction of the peroxidase enzyme with the chemiluminescent substrate, wherein the output light signal correlates with the presence/amount of the analyte of interest.

11. The method according to claim 10, wherein the concentration of the chemiluminescent cyclic diacyldihydrazide in the chemiluminescent substrate is comprised between 0.01 mM and 10 mM.

12. The method according to claim 10, wherein the concentration of the anionic N-alkylphenoxazine enhancer in the chemiluminescent substrate is comprised between 0.01 and 3 mM.

13. The method according to claim 10, wherein the concentration of the co-enhancer in the chemiluminescent substrate is comprised between 0.05 and 25 mM, preferably between 0.1 and 12 mM.

14. The method according to claim 10, wherein the concentration of the peroxide in the chemiluminescent substrate is comprised between 0.1 and 8 mM.

15. The method according to claim 10, wherein the pH of the chemiluminescent substrate is comprised between 6.0 and 9.5, preferably between 6.5 and 9.0.

16. The method according to claim 10, wherein the chemiluminescent substrate, having a pH comprised between 6.0 and 9.5, contains:
  i) the chemiluminescent cyclic diacyldihydrazide in a concentration between 0.01 mM and 10 mM;
  ii) the anionic N-alkylphenoxazine enhancer in a concentration between 0.01 and 3 mM;
  iii) the co-enhancer in a concentration between 0.05 and 25 mM; and
  iv) the peroxide oxidizer in a concentration between 0.1 and 8 mM.

* * * * *